United States Patent [19]

Hermes

[11] Patent Number: 5,248,761
[45] Date of Patent: Sep. 28, 1993

[54] AMINO ACID TERMINATED POLYESTERS HAVING PREDETERMINED MONOMERIC SEQUENCE

[75] Inventor: Matthew E. Hermes, Easton, Conn.

[73] Assignee: United States Surgical Corporation, Norwalk, Conn.

[21] Appl. No.: 929,704

[22] Filed: Aug. 12, 1992

[51] Int. Cl.$^5$ ............................................. C08G 69/00
[52] U.S. Cl. ................................... 528/361; 528/271; 528/357; 606/228; 606/230
[58] Field of Search ...................... 528/44, 45, 68, 70, 528/74, 85, 86, 271, 310, 332, 350, 354, 357, 361, 363, 370; 606/228, 230

[56] References Cited

U.S. PATENT DOCUMENTS

| | | | |
|---|---|---|---|
| 3,773,737 | 11/1973 | Goodman et al. | 528/354 |
| 3,960,152 | 6/1976 | Augurt et al. | 528/354 |
| 4,243,775 | 1/1981 | Rosensaft et al. | 525/415 |
| 4,441,496 | 4/1984 | Shalaby et al. | 528/354 X |
| 4,481,353 | 11/1984 | Nyilas et al. | 528/303 |
| 4,737,550 | 4/1988 | Tomalia et al. | 528/363 |
| 4,857,599 | 8/1989 | Tomalia et al. | 528/363 |
| 4,916,193 | 4/1990 | Tang et al. | 528/354 |
| 4,916,209 | 4/1990 | Fung et al. | 528/403 |
| 4,920,203 | 4/1990 | Tang et al. | 528/354 |
| 4,994,551 | 2/1991 | Fung et al. | 528/354 |
| 5,041,516 | 8/1991 | Frechet et al. | 528/363 |
| 5,066,772 | 1/1991 | Tang et al. | 528/354 |
| 5,120,802 | 6/1992 | Mares et al. | 528/354 |
| 5,145,945 | 9/1992 | Tang et al. | 528/354 |
| 5,152,781 | 10/1992 | Tang et al. | 528/354 |

OTHER PUBLICATIONS

Goodman et al., Polydepsipeptides I. Synthesis and Characterization of Copolymers of α-Amine and α-Hydroxy Acids, Israel Journal of Chemistry, vol. 10, pp. 867-879 (1972).

Goodman et al., Polydepsipeptides II: Synthesis and Preliminary Conformational Studies of an Alternating α-Amino and α-Hydroxy Acid Polymer, Israel Journal of Chemistry, vol. 12, Nos. 1-2, pp. 67-77 (1974).

Ingwall et al., Polydepsipeptides. III. Theoretical Conformational Analysis of Randomly Coiling nad Ordered Depsipeptide Chains, Macromolecules, vol. 7, No. 5, pp. 598-605 (1974).

Ingwall et al., Polydepsipeptides. 5. Experimental Conformational Analysis of Poly(L-alanyl-L-lactic acid) and Related Model Compounds, Macromolecules, vol. 9, No. 5, pp. 802-808 (1976).

Mathias et al., Polydepsipeptides. 6. Synthesis of Sequential Polymers Containing Varying Ratios of L-Alanine and L-actic Acid, Macromolecules, vol. 11, No. 3, pp. 534-539 (1978).

Goodman, Matrix-Controlled Synthesis and Conformational Studies of Polydepsipeptides, Journal of Polymer Science: Polymer Symposium 62, 173-188 (1978).

*Primary Examiner*—John Kight, III
*Assistant Examiner*—Shelley A. Dodson
*Attorney, Agent, or Firm*—Thomas R. Bremer; Peter G. Dilworth; Rocco S. Barrese

[57] ABSTRACT

Compositions comprising amino acid terminated polyesters having predetermined monomeric sequence are produced by stepwise addition of monomeric hydroxyacids to an amine to form a growing polymeric chain. Included herein are various amino acid terminated polyesters having predetermined monomeric sequence, methods for their production and use as well as articles formed from said compositions.

44 Claims, 1 Drawing Sheet

AMINO ACID TERMINATED POLYESTERS HAVING PREDETERMINED MONOMERIC SEQUENCE

BACKGROUND OF THE INVENTION

1. Field of the Invention

The present invention relates to amino acid terminated polyesters having predetermined monomeric sequence, methods of producing amino acid terminated polyesters having predetermined monomeric sequence and various articles produced from amino acid terminated polyesters having predetermined monomeric sequence. More particularly, amino acid terminated hydroxyacid polymers having precisely defined sequences are produced according to the present invention.

2. Description of Related Art

Hydrolyzable polyesters such as those derived from polyhydroxyacids have many important applications as biodegradable polymers. The simplest poly($\alpha$-hydroxyacid), polyglycolic acid has been successfully used as a bioabsorbable implant material in surgical procedures. Likewise, polylactic acid has been used as a bioabsorbable implant material, either by itself or as a copolymer with glycolic acid. Other hydroxyacids, e.g., hydroxybutyric acid have also been utilized.

Polyglycolic acid is generally prepared from the cyclic diester of glycolic acid (glycolide) by ring opening addition polymerization in the presence of a catalyst. In a similar manner, polylactic acid can be obtained from the cyclic diester of lactic acid (lactide) by stannous octoate-catalyzed ring opening polymerization.

Copolymers of glycolic acid and lactic acid have been developed in an attempt to combine the characteristics of both compounds and extend the range of polymer properties and rates of hydrolysis. For example poly-L-lactic acid is hydrolyzed more slowly than polyglycolic acid and copolymers of the two acids can be made to hydrolyze at intermediate rates.

Poly(lactide-co-glycolide) polymers are heterogeneous, i.e., they are made up of a random sequence of lactate and glycolate dimers. Ordinarily, properties of such copolymers are based, in part, upon the concentration of lactide and glycolide present in the starting reaction mixture. The formation of the copolymer is complicated by the fact that depending upon the catalyst used and other reaction conditions, the relative rates of reactivity of glycolide and lactide are different. For example, when equimolar amounts of glycolide and lactide are reacted, glycolide is initially more likely to combine with growing chains than is lactide. Consequently, the initial composition of the growing chain contains a predominance of glycolic acid units occasionally and randomly interspersed with short sequences of lactic acid units. As the reaction proceeds, the concentration of lactide contained in the mixture increases relative to glycolide and the ratio of glycolic acid units to lactic acid units forming the chain becomes more equal. As the reaction nears completion, most available glycolide has polymerized and the relative amount of lactide is high. Consequently, a larger number of lactic acid units are likely to come together and polymerize. Thus, the first portion of the copolymer chain is likely to contain a predominance of glycolic acid units, and the end portion of the chain is likely to contain a predominance of lactic acid units.

The random sequence generated by the synthesis of poly(lactide-co-glycolide) results in the formation of heterogeneous polymers, i.e., no two polymeric chains are likely to be identically duplicated. Consequently, the physical and chemical properties of such copolymers are difficult to predict or control with a high degree of precision. The ability to control synthesis of the precise compositional sequence of poly(lactide-co-glycolide) polymers would allow the physical and chemical properties of the polymeric products to be fixed to a high degree of certainty and allow the production of homogeneous polymers. For example, such control would allow polymers to be engineered to more precisely fit specific specifications such as degree of crystallinity and/or rates of hydrolysis.

It has been reported that pure polyglycolide is about 50% crystalline and pure poly-L-lactide is about 37% crystalline. See Gilding et al., Biodegradable Polymers for Use in Surgery, Polymer, 20:1459-1464 (1979). Gilding et al. also reported that poly(lactide-co-glycolide) polymers are amorphous between the compositional range of from 25 to 75 mole percent glycolide. For crystallinity to occur, extensive lengths of the chain need steric regularity which may be achieved with precise sequence control.

Precise control over the sequential arrangement of poly(lactide-co-glycolide) also would allow control over the rate of hydrolysis of the copolymer. The rate of hydrolysis of a glycolic acid-glycolic acid bond is greater than the rate of hydrolysis of lactic acid-glycolic acid bond which is greater than the rate of hydrolysis of a glycolic acid-lactic acid bond which is greater than the rate of hydrolysis of a lactic acid-lactic acid bond. Thus, in the copolymer segment:

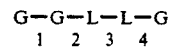

wherein glycolide is oriented to provide a hydroxy terminus on the left-most portion of the segment, i.e., HOCH$_2$CO$_2$CH$_2$... COOH, the order of hydrolysis is 1>4>2>3, i.e, 1 is fastest and 3 is slowest. Therefore, an engineered arrangement of sequential units would allow control over the rate at which a copolymer hydrolyzes.

U.S. Pat. No. 3,960,152 (the "'152 patent") describes an attempt to provide a copolymer having a controlled sequence of alternating units of lactic acid and polyglycolic acid. According to the '152 patent, lactic acid and glycolic acid are formed into a cyclic diester (3-methyl-1,4-dioxane-2,5-dione). When the cyclic diester is opened and added to a polymer chain, the lactic acid unit and glycolic acid unit are said to be adjacent in the polymer chain. However, there is no way to control the ring opening polymerization such that the ring opens at the same position every time. Thus, the ring opening and subsequent addition cannot be strictly uniform and the final product does not contain regularly alternating lactic acid units and glycolic acid units, i.e., the resulting polymer is not homogeneous.

Polydepsipeptides are copolymers of $\alpha$-amino and $\alpha$-hydroxycarboxylic acids with neighboring monomers linked either by an amide or an ester bond. Such copolymers are described as appropriate models for the conformational and optical properties of polypeptides and proteins. See, e.g., Goodman et al., Polydepsipeptides II: Synthesis and Preliminary Conformational Studies of an Alternating $\alpha$-Amino and $\alpha$-Hydroxy Acid Polymer, Israel Journal of Chemistry, 12:66-77

(1974) or Mathias et al., Polydepsipeptides.6. Synthesis of Sequential Polymers Containing Varying Ratios of L-Alanine and L-Lactic Acid, Macromolecules, 11No. 3: 534-539 (May-June 1978). In these references, no more than two adjacent lactic acid residues were esterified with alanine to form polydepsipeptides for the purpose of allowing qualitative evaluation of the helix disrupting ability of two adjacent lactic acid residues.

It would be advantageous to construct a polyester having a predetermined sequence of structural units by controlling the precise sequential arrangement of monomers in a polyester chain.

SUMMARY OF THE INVENTION

The present invention involves amino acid terminated polyesters having predetermined monomeric sequence produced by the stepwise addition of monomeric units to a growing polymeric chain. The first monomer in the chain is an N-protected, or in an alternative embodiment, a C-protected amino acid which is coupled with hydroxyacids such as glycolic acid, lactic acid, hydroxybutyric acid, tartronic acid or citric acid to form carefully regulated sequences. The resulting amino acid terminated polyesters having predetermined monomeric sequence have precisely engineered sequential arrangements which allow control over their molecular weight, rates of hydrolysis, crystallinity and other associated chemical and physical properties.

Preparation of amino acid terminated polyesters having predetermined monomeric sequence according to the present invention may be commenced by masking or blocking the amino function of an amino acid. Dimer formation is accomplished by esterification with an optionally carboxyl-protected first hydroxyacid. If protected, the carboxyl group of the first hydroxyacid may then be deprotected to allow subsequent addition of a second optionally carboxyl-protected hydroxyacid. Stepwise addition of further optionally carboxyl protected hydroxyacids allow the sequence of the resulting amine initiated homogeneous sequential polyesters to grow and be carefully regulated. Amino acids may optionally be cleaved from the amino acid terminated polyesters having predetermined monomeric sequence to form polyesters having a predetermined monomeric sequence.

Branched polyesters such as dendritic polymers can be manufactured by incorporation of hydroxy polycarboxylic acids such as tartronic acid or citric acid into growing amino acid terminated polyester chains having predetermined monomeric sequence.

Amino acid terminated polyesters having predetermined monomeric sequence can be produced by solid phase synthesis. The carboxyl group of an amino acid is covalently bonded to a resin support to allow formation of a peptide bond and addition of a first hydroxyl-protected hydroxyacid. To allow subsequent addition of a second hydroxyl-protected hydroxyacid, the hydroxyl group on the first hydroxyacid must be deprotected. Stepwise addition of further hydroxyl-protected hydroxyacids in the same manner allows the sequence to grow and be carefully regulated. Solid phase sequential polester synthesis is amenable to automation.

The present invention provides amino acid terminated polyesters having predetermined monomeric sequence, methods of making amino acid terminated polyesters having predetermined monomeric sequence, articles formed from amino acid terminated polyesters having predetermined monomeric sequence, methods of using such articles, and polyesters having predetermined monomeric sequence derived from amino acid terminated polyesters having predetermined monomeric sequence.

DETAILED DESCRIPTION OF THE INVENTION

Figure 1:
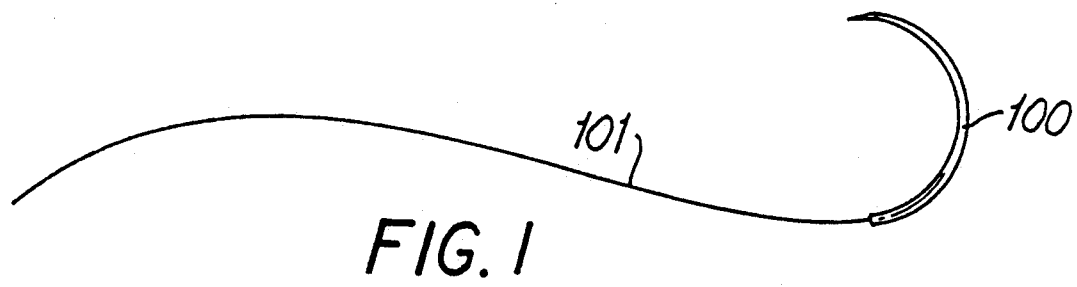
FIG. 1 is a depiction of a suture according to the present invention attached to a needle.

Amino acid terminated polyesters having predetermined monomeric sequence according to the present invention are those polyesters which contain an amino acid group and have a precise sequential monomeric order. The ability to engineer the precise chain sequence and length permits regulation of chemical and physical properties such as crystallinity, rates of hydrolysis and molecular weight of resulting polymers. As used herein, the terms "amino acid terminated polyesters having predetermined monomeric sequence" and "amine terminated sequential polyesters" are equivalent and are used interchangeably.

Generally speaking, the common available reactive sites of an amino acid are the carboxyl group and the amino group and the common available reactive sites of a hydroxyacid molecule are the carboxyl group and the hydroxyl group. Amino acid terminated polyesters having predetermined monomeric sequence in accordance with the present invention are made by placing protecting groups on all available reactive sites except those necessary to form the desired amide bond or ester bond between successive monomers. In this manner the sequential arrangement of the polymers is carefully regulated by stepwise addition of predetermined monomeric units.

Amino acids which are useful according to the present invention are represented by the formula

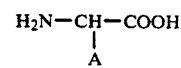

and include but are not limited to all twenty naturally occurring amino acids that are known. A represents each of the twenty known side chains that are associated with naturally occurring amino acids. Suitable amino acids herein do not inhibit polymerization to an unacceptable degree. If the amino acid terminated polyester having predetermined monomeric sequence is meant to be hydrolyzable, the amino acid should not inhibit degradation of the polymer to an unacceptable degree. Preferred amino acids are those having nonpolar side chains, the most preferred being glycine, alanine and valine. It should be understood that these examples are merely illustrative and that any amino acid capable of forming an amide bond with a hydroxyacid under appropriate conditions is within the scope of the present invention.

Hydroxyacids which are useful according to the present invention may be represented by the formula R—COOH wherein R is a hydroxyl containing, essentially hydrocarbonaceous moiety. By the phrase "essentially hydrocarbonaceous", it is meant that R may contain hetero atoms provided they do not inhibit polymerization to an unacceptable degree. If the amino acid terminated polyester having predetermined monomeric sequence is meant to be hydrolyzable, such hetero atoms do not inhibit degradation of the polymer to an unacceptable degree. If the amino acid terminated polyester having predetermined monomeric sequence is meant to be implantable, such hetero atoms do not give rise to toxic degradation products which may be difficult to metabolize.

Suitable hydroxyacids include α-hydroxyacids such as glycolic acid, lactic acid, and α-hydroxyisobutyric acid; β-hydroxyacids such as β-hydroxybutyric acid; γ-hydroxyacids such as γ-hydroxyvaleric acid; and hydroxy polycarboxylic acids such as citric acid and tartronic acid. Preferred hydroxyacids in accordance with the present invention are α-hydroxyacids while the most preferred hydroxyacids are glycolic acid, lactic acid and tartronic acid. It should be understood that these examples are merely illustrative and that any hydroxyacid capable of esterification is within the scope of the present invention.

In synthesizing amino acid terminated polyesters having predetermined monomeric sequence the amino group of the amino acid may be masked or protected. Such methods of protection are well-known in the art. Examples of amino blocking substituents include benzyloxycarbonyl (Z), t-butyloxycarbonyl (Boc), adamantyloxycarbonyl (Adoc), o-nitrophenylsulfenyl (Nps), triphenylmethyl (Trt), trifluoroacetyl (Tfa), p-toluenesulfonyl (tosyl) and methylsulfonylethyloxycarbonyl (Msc). The preferred amino blocker is t-butyloxycarbonyl (Boc). Any amino blocker is suitable for practicing the method disclosed herein as long as protection and/or deprotection is accomplished in such a manner as to not adversely effect formation of the polymer chain. Thus, removal of the blocker should not lead to destruction of the polymer or the production of side products that would interfere with the overall process.

In accordance with the present invention, after the amino group of the amino acid has been protected, the amino acid is ready to be esterified to a first hydroxyacid. In one embodiment, the reactivity of the carboxyl group of the first hydroxyacid is suppressed. In an alternative embodiment, the carboxyl group of the hydroxyacid is not blocked and remains a free acid. When the carboxyl group is blocked, only the hydroxyl group of the first hydroxyacid is available to react with the carboxyl group of the amino acid. The carboxyl group of the first hydroxyacid may be masked by ester formation, e.g., methyl, ethyl, t-butyl and benzyl ester derivatives. Any carboxyl protecting group is suitable for practicing the method disclosed herein as long as protection and/or deprotection is accomplished in such a manner as to not effect formation of the polyester chain. Thus, removal of the carboxyl protecting group should not lead to removal of the amino blocking group or destruction of the polyester or the production of side products that would interfere with the overall process. The most preferred carboxyl protecting groups are benzyl esters.

The amino-protected amino acid is then reacted with the first carboxyl-protected hydroxyacid in the presence of a dehydrating agent to yield a dimer ester. Examples of useful dehydrating agents which promote esterification include dicyclohexylcarbodiimide (DCDI), trifluoroacetic anhydride, and N,N'-carbonyldiimidazole (CDI). The preferred dehydrating agents is DCDI.

A second hydroxyacid, which may be the same or different than the first hydroxyacid, is then reacted with the first hydroxyacid to form a trimer. The carboxyl group of the second hydroxyacid may optionally be masked prior to reaction with the first hydroxyacid. In an alternative embodiment discussed below, esterification of subsequent hydroxyacids may be accomplished without blocking the carboxyl group of subsequent hydroxyacids when DCDI is used as both a protecting group and a dehydrating agent. Any protecting group which masks the carboxyl group on the first hydroxyacid must be removed before reactions to add subsequent monomers can proceed. Such removal is accomplished by means which are known to those with skill in the art. For example, a benzyl ester is removed by exposure to $H_2$ and Pd in methanol to yield the free acid. As above, formation of the ester bond between the first and second hydroxyacids is promoted by a dehydrating agent.

As was stated above, esterification may proceed without blocking the carboxyl group of hydroxyacids when DCDI is used as a dehydrating agent. The reaction may be illustrated as follows:

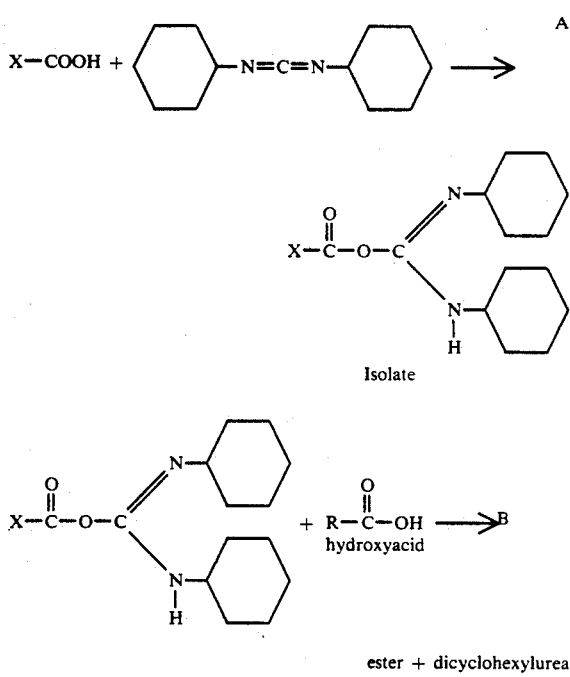

ester + dicyclohexylurea wherein X is a blocked amino containing moiety such as a blocked amino acid, or a blocked amino amide/hydroxyacid moiety and R is a hydroxyl containing, essentially hydrocarbonaceous moiety. In this reaction, DCDI may be considered to be a protecting group.

If desired, a third hydroxyacid, which may be the same or different than either the first or second hydroxyacid, is then reacted with the second hydroxyacid to form a tetramer. As with addition of the second hydroxyacid, the carboxyl group of the third hydroxyacid is optionally masked prior to reaction with the second hydroxyacid. Any protecting group which masks the carboxyl group on the second hydroxyacid must be removed before reactions to add subsequent monomers can proceed. Such removal is accomplished as above.

In accordance with the present invention, successive hydroxyacids can be added as described above to form pentamers, hexamers, etc. In this manner, the controlled addition of selected hydroxyacids yields polymer chains having precisely defined monomeric sequences. The reaction sequence is illustrated below in relation to αhydroxyacids and formation of an amine terminated trimer. As used below, A is a side chain normally associated with amino acids, $R^1$ and $R^2$ may be the same or different and are essentially hydrocarbonaceous moieties.

most preferred carboxyl protecting groups are benzyl and t-butyl ester derivatives.

The carboxyl-protected amino acid is then reacted with a first hydroxyacid having a protected hydroxyl group. Thus, the carboxyl group of the first hydroxyacid is free to form an amide bond with the protected

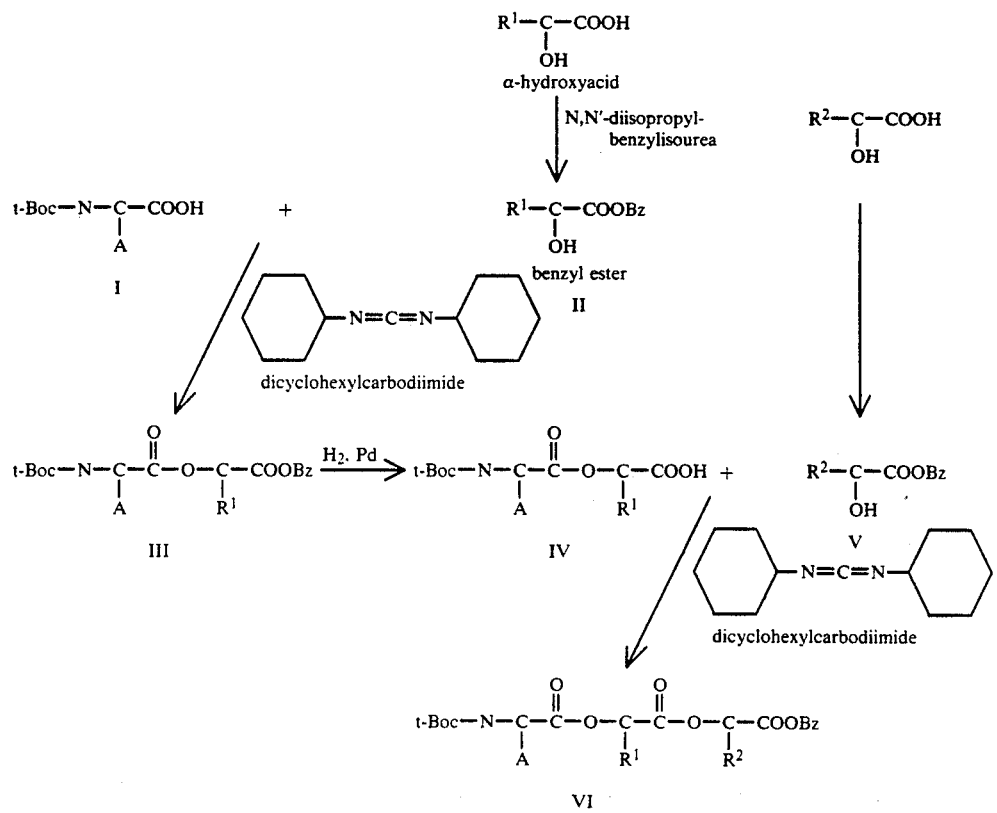

amino acid in the presence of a dehydrating agent. Any of the above described dehydrating agents are suitable for forming the amide bond between the amino acid and the first hydroxyacid.

When the polymer has reached a predetermined length and no further additions are desired, the carboxyl protecting group is removed from the final hydroxyacid by such methods as are known to those with skill in the art, e.g., $H_2$, Pd. The amino group blocking substituent may also be removed by known methods. For example the t-Boc group is removed by mild acids such as dilute HCl, in a variety of organic solvents or trifluoroacetic acid in methylene chloride. The amino acid terminus may optionally be removed from the polyester chain by such means as are known in the art. The polymer is then ready to undergo further processing and be formed into a desired shape.

In an alternative embodiment, an amine initiated homogeneous sequential polyester is synthesized by first protecting the carboxyl group of the amino acid, thus leaving the amino group as the sole reactive site. Methods of protecting a carboxyl group are well known in the art. Any carboxyl protecting group is suitable for practicing the method herein as long as protection and/or deprotection is accomplished in such a manner as to not substantially interfere with formation of the polyester chain. Thus, removal of the carboxyl protecting group should not lead to destruction of the polyester or the production of side products that would interfere with the overall process. The carboxyl group of the amino acid may be masked by ester formation, e.g., methyl, ethyl, t-butyl and benzyl ester derivatives. The The hydroxyacid may be protected with any hydroxyl protecting group as long as protection and/or deprotection is accomplished in such a manner as to not substantially adversely effect formation of the amide/polyester chain. Thus, removal of the hydroxyl protecting group should not lead to destruction of the amide/polyester or the production of side products that would interfere with the overall process.

Suitable hydroxyl protecting groups and methods of protection are described in "Protective Groups in Organic Synthesis" by Theodora W. Green, John Wiley & Sons, N.Y., 1981, whose contents are incorporated herein by reference. Hydroxyl group protection can occur, e.g., by formation of methoxymethyl ethers, t-butoxymethyl ethers, methoxyethoxymethyl ethers, bis(2-chloroethoxy) methyl ethers, 2-(trimethylsilyl) ethoxymethyl ethers, tetrahydropyranyl ethers, 4-methoxytetrahydropyranyl ethers, tetrahydrofuranyl ethers, 1-ethoxyethyl ethers, 1-methyl-1-methoxyethyl ethers, 1-(isopropoxy) ethyl ethers, trimethylsilyl ethers, triethylsilyl ethers, t-butyldimethylsilyl ethers, formate esters, benzyl formate esters, chloroacetate esters, dichloroacetate esters and other selected esters. Preferred hydroxyl protecting groups according to the present invention form tetrahydropyranyl ethers, 1- ethyoxy-ethyl esters and 1-methyl-1-methoxyethyl ethers, while the most preferred hydroxyl protecting groups form tetrahydropyranyl ethers. Various methods of deprotecting the aforesaid hydroxyl groups are known by those with skill in the art and described, e.g., by Green in the above noted reference.

A second hydroxyacid, which may be the same or different than the first hydroxyacid, may then be reacted with the first hydroxyacid in the presence of a dehydrating agent to form an ester bond. In order to accomplish such esterification, the hydroxyl protecting group must be removed from the first hydroxyacid thus leaving the hydroxyl group free to react with the free carboxyl group of the second hydroxyacid. Removal of hydroxyl protecting groups is well known in the art, e.g., by mild acid hydrolysis. The hydroxyl group of the second hydroxyacid may optionally be masked, as above, in order for the reaction to proceed without formation of unwanted side chains.

Successive hydroxyacid molecules may then be added in stepwise fashion. For example, a tetramer may be formed by adding a third hydroxyacid, which may be the same or different than either the first or second hydroxyacid, to the growing chain. The hydroxyl group of each successive hydroxyacid may optionally be masked to allow the formation of precisely engineered amine initiated homogeneous sequential polyesters. Before the third or more hydroxyacids are sequentially added, if protected, the hydroxyl group of each previously esterified hydroxyacid must be deprotected to allow ester bond formation with the next hydroxyacid. Deprotection of the masked hydroxyl groups may be accomplished as described above.

When the polymer has reached a predetermined length and no further additions are desired, the hydroxyl protecting group is removed from the final hydroxyacid in the chain by such methods as are described above. Similarly, the carboxyl protecting group may be removed from the amino acid monomer, as described above, to yield an amino acid terminated polyester having predetermined monomeric sequence.

In accordance with another aspect of the present invention, amino acid terminated polyesters having predetermined monomeric sequence may be formed by automated solid phase synthesis. Solid phase synthesis of amino acid terminated polyesters having predetermined monomeric sequence is based upon the covalent attachment of a growing amine initiated ester chain to an insoluble polymeric support or resin carrier so that unreacted reagents can be removed by filtration or washing. After the chain has been established, the amino acid terminated sequential polyester is removed from the support under conditions which do not adversely effect the polyester.

To accomplish solid phase amino acid terminated sequential polyester synthesis, the carboxyl group of a suitable amino acid is covalently bonded to an insoluble resin support via a bifunctional spacer. The insoluble support is functionalized with a functionalizer such as chloromethyl, aminomethyl or benzhydrylamino groups. One end of the bifunctional spacer reacts with the resin bound functionalizer and the other end reacts with the free carboxyl group of an amino-protected amino acid to form a covalently bonded amino acid/polymer complex.

The resin support may be a polystyrene suspension polymer cross-linked with 1% of M-divinylbenzene. Solid phase synthesis is known in relation to synthesizing sequential peptides. An overview of techniques and materials used in solid phase peptide synthesis, including means for automating such synthesis, is provided in the Encyclopedia of Polymer Science and Engineering, Vol. 12, pp. 811–858 (1988), whose contents are incorporated herein by reference. Such techniques are adaptable to synthesis of amine initiated sequential polyesters in accordance with the present invention.

The amino group of the first amino acid is masked as above with protecting groups such as benzyloxycarbonyl (Z), t-butyloxycarbonyl (Boc), adamantyloxycarbonyl (Adoc), o-nitrophenylsulfenyl (Nps), triphenylmethyl (Trt), trifluoroacetyl (Tfa), p-toluenesulfonyl (tosyl) and methylsulfonylethyloxycarbonyl (Msc). The preferred amino blocker is t-butyloxycarbonyl (Boc). Any amino blocker is suitable for practicing the method disclosed herein as long as protection and/or deprotection is accomplished in such a manner as to not adversely effect formation of the polymer chain. Thus, removal of the blocker should not lead to destruction of the polymer or the production of side products that would interfere with the overall process. After protecting the amino group, the free carboxyl group of the amino acid is covalently bonded to the resin support by procedures well known in the art.

Before addition of a hydroxayacid can proceed, the masked amino group must be deprotected by removal of the amino group blocking substituent. The amino group blocking substituent may be removed by any known method. For example, the t-Boc substituent may be removed by mild acids such as dilute HCl, in a variety of organic solvents or trifluoroacetic acid in methylene chloride.

A first hydroxyacid is then reacted with the deprotected amino acid in the presence of a dehydrating agent to form an amide bond and begin chain formation. Before forming the amide bond, the hydroxyl group of the first hydroxyacid is protected by a suitable protecting group. By leaving the carboxyl group available as the only reactive site formation of undesirable side chains is avoided.

The hydroxyl group of the first hydroxyacid is masked with protecting groups as above, i.e., as described in "Protective Groups in Organic Synthesis" by Theodora W. Green, John Wiley & Sons, N.Y., 1981, supra. Preferred protecting groups according to the present invention form tetrahydropyranyl ethers, 1-ethoxy-ethyl ethers and 1-methyl-1-methoxyethyl ethers, while the most preferred hydroxyl protecting groups form tetrahydropyranyl ethers.

Any hydroxyl protecting group is suitable for practicing the method disclosed herein as long as protection and/or deprotection is accomplished in such a manner as to not adversely effect formation of the amide/polyester chain. Thus, removal of the protective group should not lead to destruction of the amide/polyester or the production of side products that would interfere with the overall process.

The deprotected amino acid is then reacted with the first hydroxyl-protected hydroxyacid to form an amine/hydroxyacid dimer. Examples of useful dehydrating agents which promote amide bond formation are dicyclohexylcarbodiimide (DCDI), trifluoroacetic anhydride, and N,N'-carbonyldiimidazole (CDI). The most preferred dehydrating agents is DCDI.

A second hydroxyacid, which may be the same or different than the first hydroxyacid, may then be reacted with the first hydroxyacid in the presence of a dehydrating agent to form an ester bond. In order to accomplish such esterification, the hydroxyl-protecting group must be removed from the first hydroxyacid in the manner described above, thus leaving the hydroxyl group free to react with the free carboxyl group of the second hydroxyacid. The hydroxyl group of the second hydroxyacid must be masked, as above, in order for the reaction to proceed without formation of unwanted side chains.

Successive hydroxyacid molecules may then be added in stepwise fashion. For example, a tetramer may be formed by adding a third hydroxyacid, which may be the same or different than either the first or second hydroxyacid, to the growing chain. In solid phase amino acid terminated sequential polyester synthesis according to the present invention, the hydroxyl group of each successive hydroxyacid must be masked to allow the formation of precisely engineered amino acid terminated polyesters having predetermined monomeric sequence. Before the third or more hydroxyacids are sequentially added, the hydroxyl group of each previously esterified hydroxyacid must be deprotected to allow ester bond formation with the next hydroxyacid. Deprotection of masked hydroxyl groups may be accomplished as described above.

When an amino acid terminated sequential polyester chain reaches the desired length, it is cleaved from the resin support and the final hydroxyl protecting group is removed. The bifunctional spacer should incorporate a smoothly cleavable protecting group on the end which bonds to the amino acid. Suitable bifunctional spacers are wellknown in the art. Cleavage reagents are known and include acids and nucleophiles.

The steps of the solid phase synthesis of an amino acid terminated polyester may be automated by employing a liquid handling system capable of storing, metering and transferring solutions to a suitable reaction vessel. Devices such as those used for solid phase synthesis of polypeptides can be adapted for use in connection with the present invention.

Dendritic polymers may also be manufactured in accordance with the present invention by incorporation of hydroxy polycarboxylic acids into a growing polyester chain. Examples of such hydroxy polycarboxylic acids include tartronic acid, malic acid, citric acid, etc. Accordingly, an amino acid terminated polyester having predetermined monomeric sequence is made in any manner disclosed above and, at a predetermined point in the growing chain, a hydroxy polycarboxylic acid is incorporated. Subsequent hydroxyacids then form branched chains which emanate from the carboxyl groups of the hydroxy polycarboxylic acid. If further branching is desired, any number of additional hydroxy polycarboxylic acids may be incorporated at any point in the branched chain to create further branching. For example:

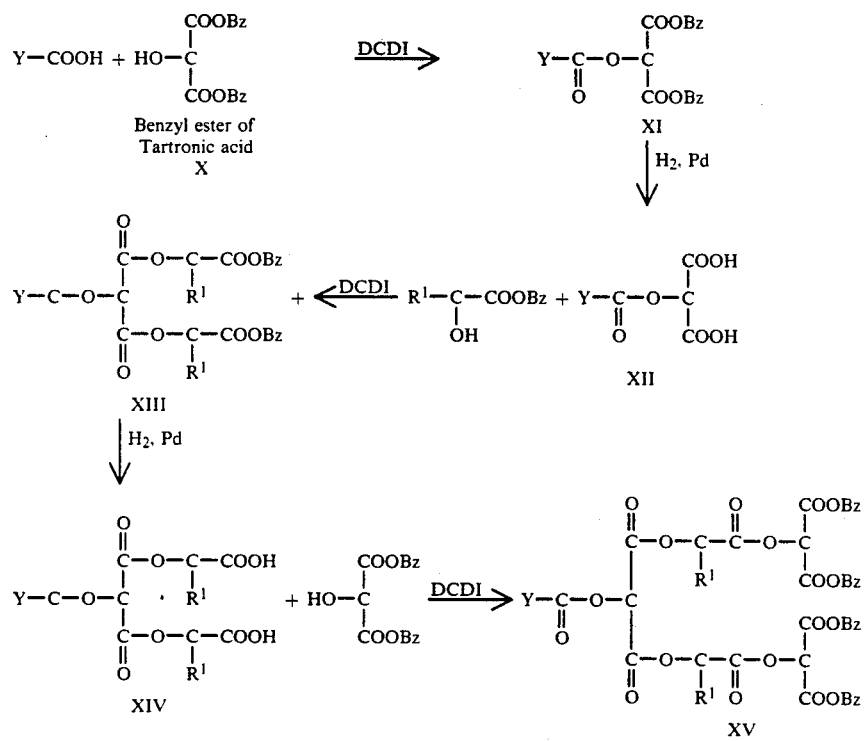

wherein Y is a portion of an amino acid terminated polyester having predetermined monomeric sequence or a polyester having predetermined primary sequence according to the present invention and $R^1$ is essentially hydrocarbonaceous.

As above, dendritic esterification may proceed without blocking the carboxyl groups of subsequently added hydroxyacids or hydroxy polycarboxylic acids by isolating resulting DCDI complexes and reacting the isolate with subsequent hydroxyacids or hydroxy polycarboxylic acids.

Amino acid terminated polyesters having predetermined monomeric sequence made in accordance with the present invention are suitable for use in a variety of applications. By varying the sequence and length of the polymer, the physical and chemical properties of the polymers can be engineered to meet predefined specifications.

The speed with which an amino acid terminated polyester having predetermined monomeric sequence degrades in an environment is based, in part, upon the rate of hydrolysis of ester bonds in the polymer chain. The present invention allows the rate of hydrolysis to be tailored in predictable fashion based upon sequence. Indeed, the exacting nature of polymers and copolymers made in accordance with present invention allows the rate of hydrolysis to be more predictable than prior random polymers and copolymers. If desired, the end portions of an amine terminated sequential polyester may be engineered to hydrolyze more quickly than the central portion of the chain.

In accordance with the present invention, thermoplastic elastomers may be constructed. Thermoplastic elastomers are multiphase compositions in which the phases are intimately dispersed. The present invention allows thermoplastic elastomers to be constructed by sequential addition of appropriate monomers to form hard and soft segments within the polymer. In addition, the amino acid terminated polyesters produced in accordance with the present invention may be combined with conventional polymers known to provide soft segments (such as, for example, polycaprolactone) or with conventional polymers known to provide hard segments (such as, for example, homopolymeric segments of glycolic or lactic acid).

Amino acid terminated polyesters having predetermined monomeric sequence according to the present invention also allow more crystalline structures to be produced. Extensive control over the chain sequence allows steric regularity to be achieved. Thus, while prior poly(lactide-co-glycolide) polymers containing 25 to 75 mole percent glycolide are amorphous, copolymers containing between 25 to 75 mole percent glycolide can be made crystalline. In this manner, the tensile strength and other physical properties can be regulated to a high degree, i.e., by varying the proportion of crystalline region to amorphous region, properties such as tensile strength and brittleness may be varied to suit particular applications.

In accordance with the present invention, oligomers of amino acid terminated sequential polyesters may be coupled to prepare larger, higher molecular weight chains of sequential polyesters. This may be accomplished by bulk polymerization of pentachlorophenol ester monomers. An inert matrix such as Celite TM diatomaceous earth may be used to enhance removal of the pentachlorophenol during thermal polymerization in vacuum and lead to higher yields and molecular weights. A p-nitrophenol ester may also be used to promote bulk polymerization. Alternatively, an amino acid terminated sequential polyester may be coupled to other polyesters to prepare larger, higher molecular weight polymers.

Amino acid terminated polyesters having predetermined monomeric sequence produced in accordance with the present invention may be used to make block copolymers. Two or more polymers prepared in accordance with the present invention may be used as the blocks and joined to form a block copolymer having highly uniform characteristics. Alternatively, one or more polymers prepared in accordance with this invention may be combined with the polymers prepared by other techniques to form block copolymers or a polymer which has an amino acid terminated polyester as a segment thereof. In addition, polymers prepared in accordance with the present invention may be blended with each other or with polymers prepared by other techniques to provide a composition having a desired set of characteristics. Methods of forming block copolymers and blends are well known in the art.

Useful products made from condensed oligomeric or polymeric amino acid terminated polyesters having predetermined monomeric sequence include fibrous surgical articles such as sutures, prosthetic ligaments, prosthetic tendons woven mesh, gauze, dressings, growth matrices and the like. Such fibrous surgical articles may be engineered to be made more or less elastic depending upon end use. Portions of a single length of monofilament can be made to hydrolyze at different rates and/or to be more or less elastic than other portions.

A suture in accordance with the present invention, suture 101, may be attached to a surgical needle 100 as shown in FIG. 1 by methods well known in the art. Wounds may be sutured by approximating tissue and passing the needled suture through tissue to create wound closure. The needle preferably is then removed from the suture and the suture tied.

Other medical articles can be manufactured from the amine terminated sequential polyesters of the present invention. These include, but are not limited to, staples, clips and other fasteners, drug delivery devices, pins, screws and other implants. Implantable surgical articles made from the polyesters of this invention may be designed to be implanted into patients where the articles are hydrolyzed and absorbed.

Drug delivery devices, as used herein, include any device or article of manufacture which is used to deliver a medicinal agent. The term "medicinal agent" is used in its broadest sense and includes any substance or mixture of substances which are useful in medicine. Thus, it is understood that a medicinal agent may be a drug, enzyme, peptide, protein, dye, or diagnostic agent such as a releasable dye which may have no biological activity per se.

Examples of various of medicinals that can be used in accordance with the present invention include antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

Amino acid terminated polyesters having predetermined monomeric sequence are well-suited for use as biodegradable polymers that are being used to address environmental concerns. For example, disposable staple items constructed from hydrolyzable homogeneous sequential polyester would biodegrade in landfills or in the ocean without leaving any toxic or non-degradable residue.

EXAMPLE 1

Construction of Carboxyl Protected Hydroxyacid

Construction of Benzyl-L-lactic Acid. L-Lactic acid (9 g, 100 mmol) is added to N,N'-diisopropylbenzylisourea (23.3 g, 100 mmol) with stirring. The mixture becomes very viscous within 10 min and is stirred intermittently for 1 h. The volume is then increased to 200 mL with THF, and the mixture stirred for 48 h at room temperature. After cooling the mixture to −15° C., the diisopropylurea is removed by filtration and the THF is evaporated under reduced pressure. The resulting thick oil is pumped under high vacuum for 24 h to give benzyl lactate (17.4 g, 95%) which may be used without further purification.

EXAMPLE 2

Construction of Carboxyl Protected Hydroxyacid

Construction of Benzyl-glycolic Acid. Glycolic acid (7.69,100 mmols) is added to N,N'-diisopropylbenzylisourea (23.39,100 mmols) with stirring for 1 hour. The volume is then increased to 200 mL with THF, and the mixture stirred for 48 h at room temperature. After cooling the mixture to $-15°$ C., the diisopropylurea is removed by filtration and the THF evaporated under reduced pressure. The resulting product is pumped under high vacuum for 24 h to give benzyl glycolate which may be used without further purification.

EXAMPLE 3

Construction of Hydroxyl Protected Hydroxyacid

Construction of the 1-ethoxyethyl ether of lactic acid. Lactic acid (7.2 g, 100 mmol) is reacted with a two fold excess of ethyl vinyl ether in dry THF in the presence of a trace of hydrogen chloride. After 16 hrs, THF and excess ethyl vinyl ether are removed under vacuum and the 1-ethoxyethyl ether of lactic acid is recovered and used without further purification.

EXAMPLE 4

Construction of Hydroxyl Protected Hydroxyacid

Construction of the 1-ethoxyethyl ether of glycolic acid. Glycolic acid (5.8 g, 100 mmol) is reacted with a two fold excess of ethyl vinyl ether in dry THF in the presence of a trace of hydrogen chloride. After 16 hrs, THF and excess ethyl vinyl ether are removed under vacuum and the 1-ethoxyethyl ether of glycolic acid is recovered and used without further purification.

EXAMPLE 5

Construction of Oligomers

Construction of Alanine-L-G-L-G-L hexamer. t-Boc-L-alanine (commercially available) is coupled to benzyl lactate with dicyclohexylcarbodiimide (DCDI) to yield t-Boc-L-alanyl-L-lactic acid benzyl ester. The benzyl ester is deprotected and made into an active acid by hydrogenation ($H_2$, Pd, methanol). The active acid is reacted with benzyl glycolate in the presence of DCDI to yield the trimer t-Boc-L-alanyl-L-lactyl-glycolic acid benzyl ester. The trimer is made into the active acid by treatment with $H_2$, Pd, methanol and coupled with DCDI to benzyl lactate. The resulting tetramer is t-Boc-L-alanyl-L-lactyl-glycolyl-L-Lactic acid benzyl ester. The tetramer is deprotected ($H_2$, Pd, methanol) and reacted with benzyl glycolate and DCDI to yield the pentamer t-Boc-L-alanyl-L-lactyl-glycolyl-L-Lactyl-glycolic acid benzyl ester. The pentamer is deprotected ($H_2$, Pd methanol) and reacted with benzyl lactate and DCDI to yield the hexamer t-Boc-L-alanyl-L-Lactyl-glycolyl-L-Lactyl-glycolyl-L-Lactic acid benzyl ester. The hexamer is deprotected at both ends by treatment with $H_2$, Pd, methanol to remove the benzyl ester and by treatment with mild acid to remove the t-Boc substituent.

EXAMPLE 6

Construction of Oligomers

Construction of glycine-L-G-G-L-L hexamer. t-Boc-L-glycine (commercially available) is coupled to benzyl lactate with DCDI to yield t-Boc-L-glycyl-L-lactic acid benzyl ester. The benzyl ester is deprotected and made into an active acid by hydrogenation ($H_2$, Pd, methanol). The active acid is reacted with benzyl glycolate in the presence of DCDI to yield the trimer t-Boc-L-glycyl-L-lactyl-glycolic acid benzyl ester. The trimer is made active by treatment with $H_2$, Pd, methanol and coupled with DCDI to benzyl glycolate to yield the tetramer t-Boc-L-glycyl-L-lactyl-glycolyl-glycolic acid benzyl ester. The tetramer is deprotected ($H_2$, Pd, methanol) and reacted with benzyl lactide and DCDI to yield the pentamer t-Boc-L-lactyl-glycolyl-glycolyl-L-lactic acid benzyl ester. The pentamer is deprotected ($H_2$, Pd, methanol) and reacted with benzyl lactide and DCDI to yield the hexamer t-Boc-L-glycyl-L-lactyl-glycolyl-glycolyl-L-lactyl-L-lactic acid benzyl ester. The hexamer is deprotected at both ends by treatment with $H_2$, Pd methanol to remove the benzyl ester and by treatment with mild acid to remove the t-Boc substituent.

The examples and embodiments depicted in this specification are not intended to be limitations of the invention described herein. Accordingly, one with skill in the art may make modifications in the products and methods of making the products which are intended to be covered by the following claims.

What is claimed is:

1. An composition comprising an amino acid terminated polyester having a predetermined monomeric sequence comprising at least one amine and at least three monomeric units derived from at least one hydroxyacid.

2. A composition according to claim 1 where said hydroxyacid monomeric units are the same or different and are selected from the group consisting of glycolic acid, lactic acid, hydroxybutyric acid, hydroxyvaleric acid, tartronic acid, malic acid and citric acid.

3. A composition according to claim 1 wherein said amino acid is selected from the group consisting of glycyl, alanyl and valyl.

4. A composition according to claim 1 wherein at least one hydroxy polycarboxylic acid is incorporated into said amino acid terminated polyester.

5. A composition according to claim 4 wherein said amino acid terminated polyester is a dendritic polymer.

6. A composition comprising a polymer having incorporated therein as a segment of said polymer an amino acid terminated polyester having a predetermined monomeric sequence.

7. A composition according to claim 6 wherein said amino acid terminated polyester is copolymerized with a polyester.

8. A composition according to claim 6 wherein said composition is a block copolymer comprising said amino acid terminated polyester.

9. A composition according to claim 8 wherein at least one block of said block copolymer comprises said amino acid terminated polyester.

10. A process for making an amino acid terminated polyester having predetermined monomeric sequence comprising stepwise addition of at least three monomeric hydroxyacid units to an amino acid monomeric unit.

11. A process for making a polymer comprising:
(a) providing an amino acid having an active site thereof protected;
(b) forming a polymer chain by the stepwise addition of at least three hydroxyacid units, the step of adding hydroxyacid units comprising:
   i) forming a reaction product including the protected amino acid, the reaction product having a terminal hydroxyacid, said terminal hydroxyacid having an active site thereof protected by a protecting substituent;
   ii) removing the protecting substituent from a terminal hydroxyacid of the reaction product; and
   iii) repeating steps (i) and (ii).

12. A process for making a polymer comprising:
(a) providing an amino acid having the amino group thereof protected;
(b) forming a polymer chain by the stepwise addition of at least three hydroxyacid monomeric units, the step of adding of hydroxyacid units comprising:
   i) forming a reaction product including the protected amino acid, the reaction product having a terminal hydroxyacid, said terminal hydroxyacid having its carboxyl group protected by a carboxyl-protecting substituent;
   ii) removing the carboxyl-protecting substituent from a terminal hydroxyacid of the reaction product; and
   iii) repeating steps (i) and (ii).

13. A process according to claim 12 wherein said step of forming a reaction product comprises reacting (i) an amino acid having an amino group protected with (ii) a first hydroxyacid having a carboxyl group protected by a carboxyl-protecting substituent whereby said first hydroxyacid becomes a terminal hydroxyacid.

14. A process according to claim 12 wherein said terminal hydroxyacid is selected from the group consisting of glycolic acid, lactic acid, hydroxybutyric acid, hydroxyvaleric acid, tartronic acid, malic acid and citric acid.

15. A process according to claim 12 wherein said terminal hydroxyacid is a hydroxy polycarboxylic acid.

16. A process according to claim 12 wherein said amino acid is selected from the group consisting of glycine, alanine and valine.

17. A process according to claim 12 wherein a carboxyl group on the terminal hydroxyacid of the reaction product and said carboxyl-protecting substituent form a member selected from the group consisting of methyl esters, ethyl esters, t-butyl esters and benzyl esters.

18. A process for making a polymer comprising:
a) providing an amino acid having the carboxyl group thereof bonded to a resin support;
b) forming a polymer chain by the stepwise addition of hydroxyacid monomeric units, the step of adding hydroxyacid units comprising;
   (i) forming a reaction product including the amino acid, said reaction product having a terminal hydroxy acid, said terminal hydroxyacid having its hydroxyl group protected by a hyroxyl-protecting substituent; the hydroxyl-protecting
   (ii) removing the hydroxyl-protecting substituent from a terminal hydroxyacid of the reaction product; and
   (iii) repeating steps (i) and (ii).

19. A process according to claim 18 wherein said step of forming a reaction product comprises reacting the amino acid with a first hydroxyacid said first hydroxyacid having its hydroxyl group protected by a hydroxyl-protecting substituent.

20. A process according to claim 18 wherein said step of providing an amino acid having the carboxyl group thereof bonded to a resin support comprises:
functionalizing an insoluble resin by reacting a functionalizer therewith;
reacting a bifunctional spacer with said functionalizer; and
reacting an amino acid with said bifunctional spacer.

21. A process according to claim 18 wherein said amino acid is selected from the group consisting of glycine, alanine and valine.

22. A process according to claim 18 wherein said terminal hydroxyacid is selected from the group consisting of glycolic acid, lactic acid, hydroxybutyric acid, hydroxyvaleric acid, tartronic acid, malic acid and citric acid.

23. A process according to claim 18 wherein said terminal hydroxyacid is a hydroxy polycarboxylic acid.

24. A process according to claim 20 wherein a hydroxyl group on the terminal hydroxyacid of the reaction product and said hydroxyl-protecting substituent form a member selected from the group consisting of methoxymethyl ethers, t-butoxymethyl ethers, methoxyethoxymethyl ethers, bis(2-chloroethoxy)methyl ethers, 2-(trimethylsilyl)-ethoxymethyl ethers, tetrahydropyranyl ethers, 4methoxytetrahydropyranyl ethers, tetrahydrofuranyl 1-ethoxyethylethers, 1-methyl-1-methoxyethyl ethers, 1-(isopropoxy)ethyl ethers, trimethylsilyl ethers, triethylsilyl ethers, t-butyl-dimethylsilyl ethers, formate esters, benzyl formate esters, chloroacetate esters, and dichloroacetate esters.

25. A process according to claim 18 further comprising the step of cleaving the amino acid terminated polyester from the support.

26. A process according to claim 18 wherein said steps (i), (ii) and (iii) are performed automatically by an automated liquid handling system.

27. A process for making a polymer comprising:
a) providing an amino acid having the carboxyl group thereof protected;
b) forming a polymer chain by the stepwise addition of hydroxyacid monomeric units, the step of adding hydroxyacid units comprising:
   (i) forming a reaction product including the protected amino acid, said product having a terminal hydroxyacid having its hydroxyl group protected by a hydroxyl-protecting substituent;
   (ii) removing the hydroxyl-protecting substituent from a terminal hydroxyacid of the reaction product; and
   (iii) repeating steps (i) and (ii).

28. A process according to claim 27 wherein said step of forming a reaction product comprises reacting said amino acid with a first hydroxyacid having a hydroxyl group protected by a hydroxyl-protecting substituent whereby said first hydroxyacid becomes a terminal hydroxyacid.

29. A process according to claim 27 wherein said amino acid is selected from the group consisting of glycine, alanine and valine.

30. A process for making an amino acid terminated polyesters having predetermined monomeric sequence according to claim 27 wherein said terminal hydroxyacid is selected from the group consisting of glycolic acid, lactic acid, hydroxybutyric acid, hydroxyvaleric acid, tartronic acid, malic acid and citric acid.

31. A process according to claim 27 wherein a hydroxyl group on the terminal hydroxyacid of the reaction product and said hydroxyl-protecting substituent form a member selected from the group consisting of methoxymethyl ethers, t-butoxymethyl ethers, methoxyethoxymethyl ethers, bis(2-chloroethoxy)methyl ethers, 2-(trimethylsilyl)ethoxymethyl ethers, tetrahydropyranyl ethers, 4-methoxytetrahydropyranyl ethers, tetrahydrofuranyl 1-ethoxyethylethers, 1-methyl-1-methoxyethyl ethers, 1-(isopropoxy)ethyl ethers, trimethylsilyl ethers, triethylsilyl ethers, t-butyl-dimethylsilyl ethers, formate esters, benzyl formate esters, chloroacetate esters, and dichloroacetate esters.

32. A process according to claim 27 wherein said step of providing an amino acid comprises reacting a carboxyl-protecting group with a carboxyl group on an amino acid to form a member selected from the group consisting of methyl esters, ethyl esters, t-butyl esters, and benzyl esters.

33. A process according to claim 27 wherein said step of forming a reaction product is conducted in the presence of a dehydrating agent selected from the group consisting of dicyclohexylcarbodiimide (DCDI), trifluoroacetic acid, and N,N'-carbonyldiimidazole (CDI).

34. A process for making a polymer comprising:
a) providing an amino acid having an amino group thereof protected;
b) forming a polymer chain by the stepwise addition of hydroxyacid monomeric units, the step of adding hydroxyacid units comprising:
  (i) forming a reaction product including the amino acid said reaction product having a terminal hydroxyacid;
  (ii) reacting the reaction product with dicyclohexylcarbodiimide to form an isolate; and
  (iii) repeating steps (i) and (ii).

35. A process as in claim 34 wherein said step of forming a reaction product comprises:
reacting said amino acid with dicyclohexylcarbodiimide to form an isolate; and
reacting said isolate with a first hydroxyacid whereby said first hydroxyacid becomes a terminal hydroxyacid.

36. A process according to claim 34 wherein said amino acid is selected from the group consisting of glycine, alanine and valine.

37. A process according to claim 34 wherein said terminal hydroxyacid is selected from the group consisting of glycolic acid, lactic acid, hydroxybutyric acid, hydroxyvaleric acid, tartronic acid, malic acid and citric acid.

38. An amino acid terminated polyester having predetermined monomeric sequence manufactured by a process of claim 10.

39. An amino acid terminated polyester having predetermined monomeric sequence manufactured by a process of claim 12.

40. An amino acid terminated polyester having predetermined monomeric sequence manufactured by a process of claim 18.

41. An amino acid terminated polyester having predetermined monomeric sequence manufactured by a process of claim 27.

42. An amino acid terminated polyester having predetermined monomeric sequence manufactured by a process of claim 34.

43. A medical device made in whole or in part of an amino acid terminated polyester having predetermined monomeric sequence.

44. A medical device according to claim 43 wherein said medical device is selected from the group consisting of sutures, prosthetic ligaments, prosthetic tendons, staples, clips, pins, screws, mesh, felt, growth supporting matrices and drug delivery devices.

* * * * *